(12) United States Patent
Yu (10) Patent No.: US 9,977,019 B2
(45) Date of Patent: May 22, 2018

(54) FLUOROUS PEPTIDE MICROARRAY, DETECTION PROCESS USING A FLUOROUS PEPTIDE MICROARRAY, AND PROCESS OF FORMING A FLUOROUS PEPTIDE MICROARRAY

(71) Applicant: MS² ARRAY LLC, Pittsburgh, PA (US)

(72) Inventor: Marvin Yu, Pittsburgh, PA (US)

(73) Assignee: MS² Array LLC, Pittsburgh, PA (US)

( * ) Notice: Subject to any disclaimer, the term of this patent is extended or adjusted under 35 U.S.C. 154(b) by 162 days.

(21) Appl. No.: 14/394,435

(22) PCT Filed: Apr. 16, 2013

(86) PCT No.: PCT/US2013/036748
§ 371 (c)(1),
(2) Date: Oct. 14, 2014

(87) PCT Pub. No.: WO2013/162948
PCT Pub. Date: Oct. 31, 2013

(65) Prior Publication Data
US 2015/0192578 A1    Jul. 9, 2015

Related U.S. Application Data

(60) Provisional application No. 61/637,978, filed on Apr. 25, 2012.

(51) Int. Cl.
*G01N 33/543* (2006.01)
*G01N 33/58* (2006.01)

(52) U.S. Cl.
CPC . *G01N 33/54386* (2013.01); *G01N 33/54306* (2013.01); *G01N 33/582* (2013.01); *G01N 2333/90* (2013.01)

(58) Field of Classification Search
None
See application file for complete search history.

(56) References Cited

U.S. PATENT DOCUMENTS

| | | | |
|---|---|---|---|
| 4,885,250 A | 12/1989 | Eveleigh et al. | |
| 4,954,444 A | 9/1990 | Eveleigh et al. | |
| 5,525,264 A * | 6/1996 | Cronin | B32B 17/06 252/583 |
| 5,777,121 A | 7/1998 | Curran et al. | |
| 5,859,247 A | 1/1999 | Curran et al. | |
| 6,156,896 A | 12/2000 | Curran et al. | |
| 6,416,818 B1 * | 7/2002 | Aikens | B82Y 30/00 427/383.1 |
| 6,673,539 B1 | 1/2004 | Wipf et al. | |
| 7,211,825 B2 * | 5/2007 | Shih | H01L 29/78633 257/13 |
| 2001/0031469 A1 | 10/2001 | Volinia | |
| 2009/0149343 A1 | 6/2009 | Nightingale | |
| 2010/0016171 A1 | 1/2010 | Wong et al. | |
| 2010/0159604 A1 | 6/2010 | Pohl et al. | |
| 2013/0115430 A1 * | 5/2013 | Ober | C12N 11/00 428/195.1 |

FOREIGN PATENT DOCUMENTS

| | | |
|---|---|---|
| WO | 2002083933 A2 | 10/2002 |
| WO | 2004035744 A2 | 4/2004 |
| WO | 2006009494 A1 | 1/2006 |
| WO | 2011109368 A2 | 9/2011 |

OTHER PUBLICATIONS

Fluorous Microarrays (Fluorous Technologies, Inc.) downloaded on Aug. 23, 2016.*
Baker et al Journal of Environmental Management Journal of Environmental Management 92 (2011) 2781—2785.*
Wang et al Surface Modification of Poly(dimethylsiloxane) with a Perfluorinated Alkoxysilane for Selectivity toward Fluorous Tagged Peptides Langmuir 2008, 24, 1080-1086.*
Fluorous Technologies Fluorous Immobilization for Microarray Formation pp. 1-2, downloaded on Jan. 4, 2017.*
Ko et al., Fluorous-Based Carbohydrate Microarrays J. Am. Chem. Soc. 2005, 127, 13162-13163.*
Electrical resistivity and conductivity From Wikipedia, the free encyclopedia pp. 1-19; downloaded on Jan. 4, 2017.*
Zhong et al Solid-Phase Synthesis of Arginine-Containing Peptides by Guanidine Attachment to a Sulfonyl LinkerJ. Org. Chem. 1997, 62, 9326-9330.*
Fluorous Microarrays (Fluorous Technologies, Inc.) downloaded on Jan. 4, 2017 pp. 1-2.*
E.P. Go, "Selective Metabolite and Peptide Capture/Mass Detection using Fluorous Affinity Tags", Journal of Proteome Research, 2007, 6, pp. 1492-1499, copyright 2007 American Chemical Society, published on Web Mar. 8, 2007.
P.H. Blit, et al., "Surface Immobilization of Elastin-like Polypeptides using Fluorinated Surface Modifying Additives", Journal of Biomedical Materials Research, Part A, vol. 96A, No. 4, Mar. 15, 2011, pp. 648-662.

(Continued)

*Primary Examiner* — Maria G Leavitt
(74) *Attorney, Agent, or Firm* — Frost Brown Todd LLC (57) ABSTRACT

A fluorous peptide microarray, a process of detecting information by using a fluorous peptide microarray, and a process of forming a fluorous peptide microarray are disclosed. The fluorous peptide microarray includes a covalently-modified conductive fluorous surface and fluorous-tagged peptides having natural amino acids positioned on the covalently-modified conductive fluorous surface. The fluorous-tagged peptides are configured for analysis of one or both of a protein and an enzyme. The process of detecting information includes using the fluorous peptide microarray. The process of forming the fluorous peptide microarray includes spotting the fluorous-modified composition to the fluorous surface after a solution phase reaction or transfer blotting the fluorous-modified composition.

15 Claims, 7 Drawing Sheets

(56) References Cited

OTHER PUBLICATIONS

C.C. Larsen et al., "The effect of RGD fluorosurfactant polymer modification of ePTFE on endothelial cell adhesion, growth and function", Biomaterials, vol. 27, No. 28, Oct. 1, 2006, pp. 4846-4855, Elsevier Science Publishers BV., Barking, GB.

D. Wang, "Surface Modification and Characterization of Poly(dimethylsiloxane) with a perfluorinated Alkoxysilane for Selectivity Towards Fluorous Tagged Peptides", Queens's University—Thesis Master of Science, May 1, 2008, retrieved from the Internet: URL:http://qspace.library.queensu.ca/bitst ream/1974/1205/1/Wang_Dan_200805_MSc.pdf, pp. 32, 33, 43, 67 and 80, figures 3.13-3.16.

A. Nordstrom et al., "Surfactant-enhanced desorption/ionization on silicon mass spectrometry, Analytical Chemistry", vol. 78, No. 1, Jan. 1, 2006, pp. 272-278, American Chemical Society.

G. MacBeath, "Printing Proteins as Microarrays for High-Throughput Function Determination", Science Magazine, Sep. 8, 2000, vol. 289, pp. 1760-1762.

P. Voigt, "Histone Tails: Ideal Motifs for Probing Epigenetics through Chemical Biology Approaches", ChemBioChem 2011, vol. 12, pp. 236-252, copyright 2011 Wiley-VCH Verlag GmbH & Co. KGaA, Weinheim.

S. Chang, "Glycan Array on Aluminum Oxide-Coated Glass Slides through Phosphonate Chemistry", Journal of American Chemical Society, 2010, vol. 132, pp. 13371-13380, copyright 2010 American Chemical Society.

Z.A. Gurard-Levin, "Combining Mass Spectrometry and Peptide Arrays to Profile the Specificites of Histone Deacetylases", ChemBioChem 2009, vol. 10, pp. 2159-2161, copyright 2009 Wiley-VCH Verlag GmbH & Co. KGaA, Weinheim.

B.Y.M. Collet, "Fluorous-based peptide microarrays for protease screening", Journal of Fluorine Chemistry, 2009, copyright 2009 Elsevier B.V.

A.J. Vegas, "Fluorous-Based Small-Molecule Microarrays for the Discovery of Histone Deacetylase Inhibitors", Angew. Chem. Int. Ed. 2007, vol. 46, pp. 1-6, copyright 2007 Wiley-VCH Verlag GmbH & Co. KGaA, Weinheim.

J. Kim, "Tudor, MBT and chromo domains gauge the degree of lysine methylation", EMBO reports vol. 7, No. 4, 2006, pp. 397-403, copyright 2006 European Molecular Biology Organization.

S. Himpel, "Specificity Determinants of Substrate Recognition by the Protein Kinase DYRK1A", The Journal of Biological Chemistry, vol. 275, No. 4, Issue of Jan. 28, pp. 2431-2438, 2000, copyright 2000 by the American Society for Biochemistry and Molecular Biology, Inc.

X. Espanel, "Mapping of Synergistic Components of Weakly Interacting Protein-Protein Motifs Using Arrays of Paired Peptides", The Journal of Biological Chemistry, vol. 278, No. 17, Issue of Apr. 25, pp. 15162-15167, 2003, copyright 2003 by the American Society for Biochemistry and Molecular Biology, Inc.

S.E. Hutchinson, "Enabling Lead Discovery for Histone Lysine Demethylases by High-Throughput RapidFire Mass Spectrometry", Journal of Biomolecular Screening, published online Aug. 21, 2011 Sage Publications, pp. 1-9.

T.R. Northen, "A Nanostructure-Initiator Mass Spectrometry-Based Enzyme Activity Assay", PNAS, Mar. 11, 2008, vol. 105, No. 10, pp. 3678-3683, www.pnas.org/cgi/doi/10.1073/pnas.0712332105.

K. Ko, "Fluorous-Based Carbohydrate Microarrays", J. Am. Chem. Soc. 2005, vol. 127, pp. 13162-13163, 2005 American Chemical Society.

S.S. Oliver, "Dynamic Interplay between Histone H3 Modifications and Protein Interpreters: Emerging Evidence for a "Histone Language"", ChemBioChem 2011, vol. 12, pp. 299-307, copyright 2011 Wiley-VCH Verlag GmbH & Co. KGaA, Weinheim.

M. Kacevska, "Perspectives on Epigenetics and its Relevance to Adverse Drug Reactions, Clinical Pharmacology & Therapeutics", vol. 89, No. 6, Jun. 2011, pp. 902-907, advance onlline publication Apr. 20, 2011, Nature Publishing Group, www.nature.com/cpt.

A. Petronis, "Epigenetics as a Unifying Principle in the Aetiology of Complex Traits and Diseases", Nature, vol. 465, Jun. 10, 2010, pp. 721-727, 2010 Macmillan Publishers Limited.

J Comley, "Epigenetics, an Emerging Target Class for Drug Screening", Drug Discovery World, Spring 2011, pp. 40-55.

A.J. Flavell, "A Microarray-based High Throughput Molecular Marker Genotyping Method: The Tagged Microarray Marker (TAM) Approach", Nucleic Acids Research, 2003, vol. 31, No. 19, pp. 1-8, Oxford University Press 2003, downloaded from http://nar.oxfordjournals.org/ at University of Pittsburgh on Apr. 3, 2012.

Y. Ito, "Solid-phase Oligosaccharide Synthesis and Related Technologies", Chemical Biology 1998, 2:701-708, http://biomednet.com/elecref/13675931002000701, Current Biology Ltd, ISSN 1367-5931.

B.B. Haab, "Methods and Applications of Antibody Microarrays in Cancer Research", Proteomics 2003, 3, 2116-2122, 2003 Wiley-VCH Verlag GmbH & Co. KGaA, Weinheim.

J.S. Shumaker-Parry, "Microspotting Streptavidin and Double-Stranded DNA Arrays on Gold for High-Throughput Studies of Protein—DNA Interactions by Surface Plasmon Resonance Microscopy", Analytical Chemistry, vol. 76, No. 4, Feb. 15, 2004, pp. 918-929, 2004 American Chemical Society, Published on Web Jan. 9, 2004.

S.M. Brittain, "Enrichment and Analysis of Peptide Subsets using Fluorous Affinity Tags and Mass Spectrometry", Nature Biotechnology, Advance Online Publication, pp. 1-6, Published online Mar. 13, 2005, 2005 Nature Publishing Group, http://www.nature.com/naturebiotechnology.

C. Beller, "Noncovalent Attachment of Nucleotides by Fluorous—Fluorous Interactions: Application to a Simple Purification Principle for Synthetic DNA Fragments", Helvetica Chimica Acta, vol. 88 (2005), pp. 171-179, 2005 Verlag Helvetica Chimica Acta AG, Zurich.

P.C. de Visser, "A Novel, Base-Labile Fluorous Amine Protecting Group: Synthesis and Use as a Tag in the Purification of Synthetic Peptides", Tetrahedron Letters 44 (2003) pp. 9013-9016, 2003 Elsevier Ltd.

Z.A. Gurard-Levin, "The Activity of HDAC8 Depends on Local and Distal Sequences of its Peptide Substrates", Biochemistry 2008, 47, 6242-6250, 2008 American Chemical Society, published on Web 05/10/2088.

B.T. Houseman, "Maleimide-Functionalized Self-Assembled Monolayers for the Preparation of Peptide and Carbohydrate Biochips", Langmuir 2003, 19, 1522-1531, 2003 American Chemical Society, published on Web Nov. 13, 2002.

M. Mrksich, "Mass Spectrometry of Self-Assembled Monolayers: A New Tool for Molecular Surface Science", ACS NANO, vol. 2, No. 1, 7-18, 2008, published online Jan. 22, 2008, www.acsnano.org, 2008 American Chemical Society.

A. Dhall, "Chemical Approaches to Understand the Language of Histone Modifications", ACS Chemical Biology, 2011, 6, 987-999, 2011 American Chemical Society.

E.P. GO, "Fluorous Based Affinity Mass Spectrometry", ASMS 2005.

* cited by examiner

FLUOROUS PEPTIDE MICROARRAY, DETECTION PROCESS USING A FLUOROUS PEPTIDE MICROARRAY, AND PROCESS OF FORMING A FLUOROUS PEPTIDE MICROARRAY

REFERENCE TO SEQUENCE LISTING

A Sequence Listing has been submitted in computer readable form (CRF) and is hereby incorporated by reference in its entirety.

FIELD OF THE INVENTION

The present invention relates to compositions, structures formed by the compositions, processes of forming the compositions and the structures, and detection processes relying upon the compositions and structures. More specifically, the present invention relates to fluorous peptide microarrays, fluorous peptide microarray detection processes, and fluorous peptide microarray compositions.

BACKGROUND

Peptides are often favored substrates for the investigation of biomolecule interactions, small molecule inhibition of such interactions, and in the elucidation of biochemical pathways. Peptides can be excellent surrogates for proteins of interest since they represent a segment of the protein but are more easily prepared, modified, and analyzed than full proteins. As such, assays and screens utilizing peptides as substrates or probes have become an integral part of the drug discovery and development process from target identification and validation through hit optimization and lead optimization. In addition, peptide-based diagnostics and therapeutics are increasing with peptide-based assays and screens playing an important role in drug development and clinical applications. The development of assays and screens using peptides as probes that provide high quality and high throughput is a continuing area of interest to the life sciences industry.

There are a number of methods used currently for peptide-based assays. The standard methods are solution-phase-based methods using microtiter plates containing a number of wells generally ranging from 96 to 1536. The test solution and compounds along with a labeled peptide probe are added to each well. The label is generally a fluorogenic or chemiluminescent label which is necessary for detection. After the reaction is complete, the plate is scanned and those reactions which were positive can be distinguished from those that are negative through the fluorescent or chemiluminescent label. Microtiter-plate-based solution phase assays can often be conducted with very high throughput resulting in large data sets that are highly data dense. The primary shortcoming of these types of assays; however, is that the data is generally not of high quality.

Low data quality is generally due to the use of the fluorescent or chemiluminescent detection label. The label itself can oftentimes interfere with the native activity or selectivity of the peptide/protein of interest. This results in a high rate of false positives and negatives. In addition, when adding test compounds that are potential drug candidates, fluorescence and chemiluminescence detection can be compromised either by autofluorescence or by interference from the test compound. It is common for 10% fluorescence interference rates to be reported when screening a library of compounds using assays of this type.

In addition, the information gathered by using fluorescent or chemiluminescent detection does not provide any structural information. Depending on the design of the assay, information such as the degree of change imparted on the peptide probe or the exact location of that change is lost. For example, in a protease screen, a variety of putative peptide substrates may be examined using a fluorogenic label. Cleavage of the peptide at the designed amino acid location results in a positive signal. However, if proteolytic activity were to take place concommitently at other sites within the peptide backbone, that would not be detected by the assay. Alternatively, if two putative sites of proteolysis were available on the peptide, a positive signal would indicate that some proteolysis took place, but would not distinguish at which location. So, while the solution-phase-based assays can often be high throughput, they suffer from producing low-quality data which often requires extensive re-testing by other methods in order to confirm the results or to obtain additional information.

In order to overcome some of the shortcomings of solution-phase assays, solid-phase assay methods have been developed. In solid-phase assays, the peptide probes are immobilized, usually through covalent bonding to a surface, for example, the bottom of a well within a microtiter plate. The peptide may or may not be labeled as in the solution-phase assay. The test solution containing the protein or enzyme, test compound, and/or other reaction components is added. Once the reaction is complete, the solution is removed and the well is washed to remove all other components leaving only the immobilized probe peptide. If the peptide was labeled, the fluorescence or chemiluminescent detection can be used as in the solution-phase assay. The major advantage of the solid-phase method is that autofluorescent of fluorescence-interfering materials can be washed away reducing the number of false readouts. This does not; however, overcome limitations due to the presence of the label itself which may interfere with the action of the protein nor does it provide additional structural information missing from the solution-phase assay.

Solid-phase assays also allow for the use of other detection methods. One known method is a radiometric method where a radioactive-isotope-labeled atom is incorporated into the peptide either before or after the desired reaction. Popular radioisotopes include $^{14}C$, $^{32}P$, $^{25}S$, and $^{152}I$. Radiometric methods are extremely sensitive and can oftentimes be quite specific. The major disadvantages are the special care and precautions necessary when using radioactive materials and the cost of the isotopes which can preclude use in early screening efforts. In addition, radiometric detection provides no structural information, such as the location of the radioisotope incorporation within the peptide, nor does it provide a reliable measure of degree of radioisotope incorporation.

Another known detection method is a coupled assay which utilizes a second reaction in order to introduce a fluorescent or chemiluminescent label. In a coupled assay, label-free peptides can be used as the probe thereby avoiding any questions as to the effect of the label on protein activity. After the desired reaction is complete, a secondary reaction, generally using a labeled specific antibody, is conducted. The specific antibody only binds to the transformation in question, thereby providing the fluorescent signal. A solid-phase assay using a coupled antibody reaction therefore overcomes the problem of the labeled peptide probe and the interference issues often associated with solution-phase assays. Once again; however, it does not provide information-rich data.

In addition, the coupled assay can require introduction of appropriate surface chemistry in order to immobilize the probes. A large number of different surface chemistries have been introduced for probe immobilization including affinity-based bonding, such as biotin-streptavidin bonding and covalent bonding, as in maleimide, Diels-Alder, click chemistry, etc. Non-specific binding is often a problem with these methods, causing binding of other molecules besides the probe molecule to the surface, thereby compromising signal to noise ratio. For example, if the antibody used in the coupled assay non-specifically binds to the surface, then a false positive signal will be received. Also, the coupled assay is dependent on the availability and selectivity of the antibody. In the absence of a highly selective antibody, the assay will once again result in a high number of false readouts. This lack of specific antibodies is in many areas including epigenetics considered to be the biggest shortcomings within the field.

Despite these drawbacks in information quality and robustness, solid-phase assays have found widespread use within the life sciences industry, primarily due to the high throughput that can be achieved, the epitome of which is the microarray where thousands of probes can be applied to a small surface and interrogated at once. Microarrays, including peptide microarrays, have been demonstrated extensively. Beyond the high throughput, the miniaturized format of microarrays allows minimal use of protein, probe, and reagents thereby reducing the overall cost per probe relative to microtiter-plate formats. The microarray format does not overcome the detection problems; however, of other assay formats.

Other label-free detection methods include optical methods, such as surface-plasmon resonance (SPR). SPR provides no structural information but is a sensitive method by which to observe changes in probes or to detect binding events. Even so, there are some transformations, such as phosphorylation, which SPR cannot reliably detect.

In order to address data quality issues, researchers have turned primarily to mass spectrometry (MS) as a label-free detection method. Mass spectrometry is particularly well-suited for peptide probes since it can not only detect both starting probes and products, but also determine the degree of change on the probe and the location of the change. One such known detection method uses histone methyltransferases (HMETs), where a lysine may be singly, doubly, or triply methylated. Another such detection method uses HMETs having various lysines reside, such as on histone 3 (H3). In this case, methylation can occur on either K4 or K9 and can be readily distinguished by MS as opposed to other methods.

While providing high quality data, MS generally suffers from being only low to medium throughput. This is due primarily to the necessary sample preparation and purification in order to remove impurities and other unwanted materials from the reaction which can adversely affect sensitivity and detection. A favored method is to use a solution-phase assay and coupled liquid chromatography and MS (LC/MS). The chromatographic separation purifies the probe of interest so that it can then be analyzed by MS. This method; however, is very low throughput with each sample requiring a minute or more of time to analyze. Other methods, such as multiplexed (MUX) electrospray with parallel LC systems, have reduced the analysis time to as short as 30 seconds/sample, but still are orders of magnitude behind other assay methods. Another recent system includes a microfluidics-based desalting system coupled with MS detection. This system has been reported to process samples at a rate of one every 5-7 seconds which is significantly higher than other MS-based methods but still falls far short of fluorescence or radiometric-based systems.

In order to try and bridge the gap between high throughput and high quality data, others have tried to combine microarrays with MS detection. The primary difficulty in combining microarrays with MS detection is that methods for immobilization of peptides generally utilize covalent bonding formed by reaction of a reactive group on the peptide and a reactive group on the surface. The covalent bond formation allows the peptide to be immobilized in a specific orientation and through a specific location on the peptide, most commonly either the C or N terminus. Most covalently bound peptides, however, cannot be ionized from the surface once the covalent bond is formed making it incompatible with direct MS detection. Non-covalent immobilization methods have also been used to form microarrays but generally lack specific display orientation which can affect substrate activity. There are, however, methods which can combine a microarray format with MS detection.

A primary example of this would be self-assembled monolayer desorption/ionization MS (SAMDI-MS) where peptides are immobilized through the formation of alkanethiol monolayers on a gold surface. The peptides can then be reacted with the test solution of interest. A chemical matrix is then added to induce ionization and the peptide probes are then analyzed by matrix-assisted laser desorption/ionization (MALDI-MS). SAMDI-MS then combines the high throughput of microarrays with the high quality data of MS detection.

The method, however, suffers from a number of deficiencies. First, results can be highly variable and dependent on the choice and application of the matrix. The optimal matrix can vary depending on the monolayer employed and the nature of the probes. Application of the matrix also needs to be precisely controlled in order to avoid inconsistencies and "patches" across the array resulting in areas of poor signal. In addition, the monolayers themselves may not be robust and are subject to degradation at elevated temperatures and upon exposure to UV light. These issues lead to questions regarding long-term storage and scalability, both critical items for commercialization.

There have recently been described efforts at avoiding some of the issues presented by SAMDI-MS. One method is to utilize fluorous immobilization where a perfluorocarbon modified surface is used to immobilize perfluorocarbon modified probes through fluorous partitioning. Fluorous-based microarrays have been formed using small molecules, peptides, and, most commonly, carbohydrates. Direct MS detection has only been demonstrated with carbohydrate arrays. Fluorous immobilization combines aspects of non-covalent and covalent immobilization. The probes are immobilized non-covalently through fluorous partitioning but in a specific display orientation through a specific end of the molecule; a characteristic usually reserved only for covalent bonding motifs. MS detection can then be conducted either through the use of a nano-structure initiated MS (NIMS) or directly off the surface, in some cases by laser ablation without the need of matrix. These non-matrix methods also have the advantage of being highly robust systems that require a minimum of special storage conditions.

A major limitation of many of these MALDI-MS or SAMDI-MS array methods is the inability to directly enrich the samples in the analytes of interest. Analyte enrichment results in greater sensitivity and higher quality spectra and is often conducted prior to array formation thereby resulting in lower throughput. In this way, one of the major advantages of MALDI or SAMDI based methods over LC/MS and microfluidic based methods can be lost.

There has been only one example of a fluorous peptide microarray and it does not utilize MS as the detection method. Nor would it be capable of doing so since all examples of fluorous microarrays with direct MS detection use either a porous surface, such as silica, or a conductive surface, such as alumina. Fluorous immobilization of peptides is not necessarily as straightforward as immobilization of carbohydrates due to the increased variability for peptides in polarity and charge states which influences fluorous partitioning. The variability in charge states is further increased when using peptides with a number of post-translational modifications. The fluorous peptide array is only capable of using fluorescent detection and suffers from all of the limitations noted earlier for fluorescence-based detection methods.

Accordingly, it would be desirable to have materials, methods, and processes that do not suffer from one or more of the above drawbacks.

SUMMARY

An exemplary embodiment of the present disclosure includes a fluorous peptide microarray having a covalently-modified conductive fluorous surface and fluorous-tagged peptides having natural amino acids positioned on the covalently-modified conductive fluorous surface. The fluorous-tagged peptides are configured for analysis of one or both of a protein and an enzyme.

Another exemplary embodiment of the present disclosure includes a process of detecting information by using a fluorous peptide microarray. The fluorous peptide microarray includes a covalently-modified conductive fluorous surface and fluorous-tagged peptides having natural amino acids positioned on the covalently-modified conductive fluorous surface. The fluorous-tagged peptides are configured for analysis of one or both of a protein and an enzyme.

Another exemplary embodiment of the present disclosure is a process of forming a fluorous peptide microarray. The process includes providing a fluorous-modified composition, the fluorous-modified composition including a linker, a peptide connected to the linker, and a fluorous domain connected to the linker. The process further includes spotting the fluorous-modified composition to the fluorous surface after a solution phase reaction or transfer blotting the fluorous-modified composition to form the fluorous peptide microarray.

Further aspects of embodiments of the invention are disclosed herein. The features as discussed above, as well as other features and advantages of the present application, will be appreciated and understood by those skilled in the art from the following drawings and detailed description.

BRIEF DESCRIPTION OF THE DRAWINGS

Wherever possible, the same reference numbers will be used throughout the drawings to represent the same parts.

DETAILED DESCRIPTION OF EXEMPLARY EMBODIMENTS

Provided is a fluorous peptide microarray, a compositional detection process, a process of forming a fluorous peptide microarray, a fluorous-modified composition, and a fluorous peptide microarray process. Embodiments of the present disclosure may permit acquisition of denser data during detection (for example, by having high throughput), may permit acquisition of more information during detection (for example, higher quality information, structural information, and/or information not available through other microarray techniques), may result in lower false readouts for detection (for example, by reducing or eliminating antibodies and other coupled reactions), may simplify workflows in the formation of arrays (for example, by eliminating blocking and washing steps or the use of an added matrix as is done in existing techniques corresponding to SAMDI), or combinations thereof.

Figure 1:
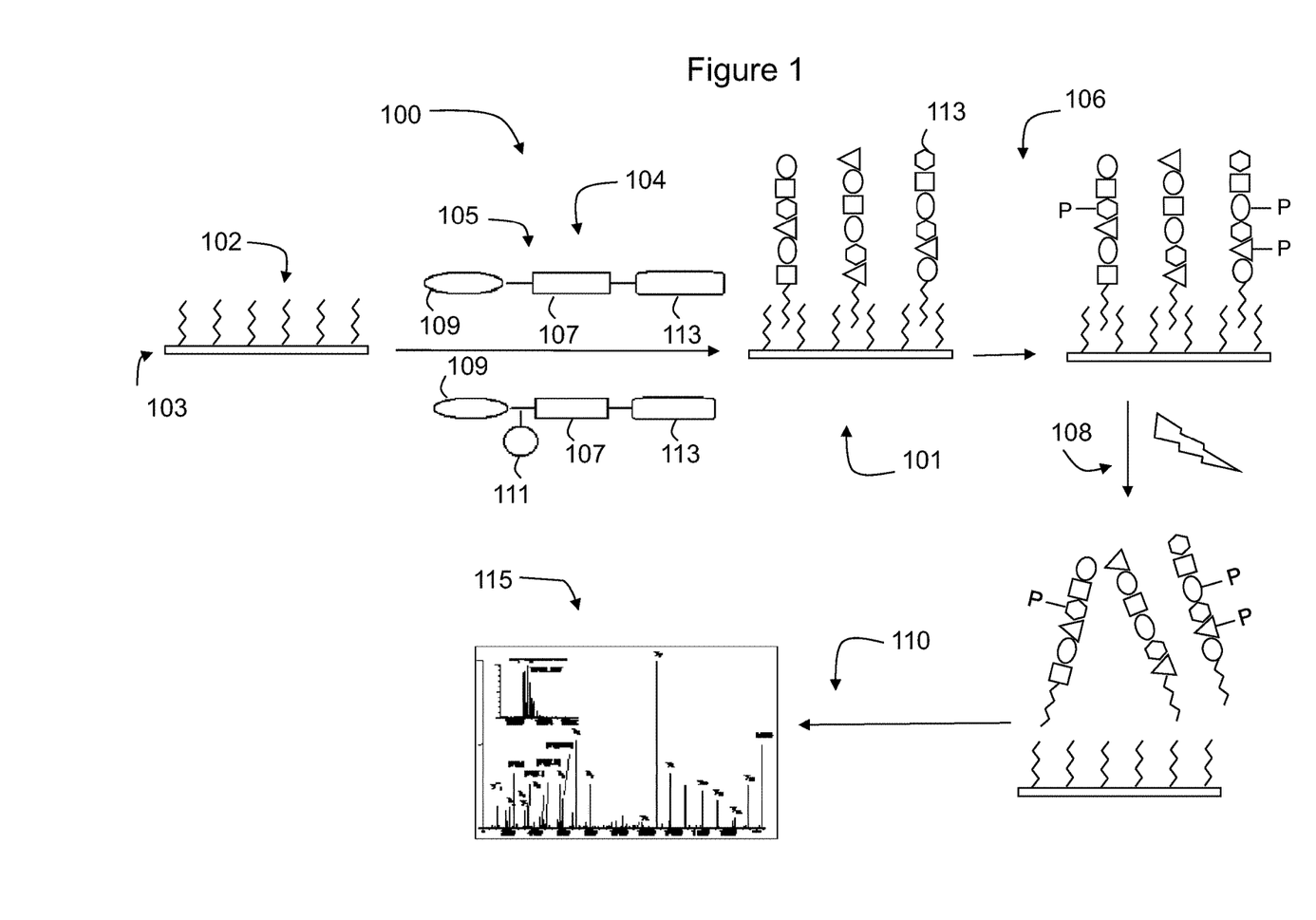
FIG. 1 shows a schematic view of an exemplary process of forming an exemplary fluorous peptide microarray according to the disclosure.

FIG. 1 shows an embodiment of a process 100 of forming a fluorous peptide microarray 101. The process 100 includes providing a covalently-modified conductive fluorous surface 103 (step 102) and applying a fluorous-modified composition 105 (step 104), such as a fluorous-tagged peptide, to the covalently-modified conductive fluorous surface 103, thereby forming the fluorous peptide microarray 101. The covalently-modified conductive fluorous surface 103 is any suitable surface, such as, a surface formed by chemical vapor deposition, for example, a fluorous-modified indium tin oxide, a fluorous-modified silicon black, or a combination thereof. The covalently-modified conductive fluorous surface is conductive with a sheet resistivity of less than 50 ohms/square.

The fluorous-modified composition 105 or a plurality of fluorous-modified compositions 105 is/are applied to the covalently-modified conductive fluorous surface 103 by, for example, spotting and/or transfer blotting. Generally, spotting includes independently preparing solutions having the fluorous-modified composition 105 and individually spotting the solutions to the covalently-modified conductive fluorous surface 103 to form the fluorous peptide microarray 101. Transfer blotting, as is further described below with reference to FIG. 4, generally includes using in situ methods, such as simultaneous peptide synthesis on membranes, known as SPOT synthesis, or peptide laser printing. In one embodiment, the transfer blotting includes attaching portions of the fluorous-modified composition 105 to peptides for form an embodiment of the fluorous peptide microarray 101 that is not immobilized by fluorous partitioning.

The covalently-modified conductive fluorous surface 103 is capable of immobilizing fluorous-modified peptides through fluorous partitioning (for example, when the peptides include a terminal fluorous tag capable of immobilizing the peptide onto the covalently-modified conductive fluorous surface 103). The immobilizing is through non-covalent fluorous partitioning resulting in specific display orientation of the peptides through either the C or N terminus of the peptide or any other suitable method.

Figure 1A:
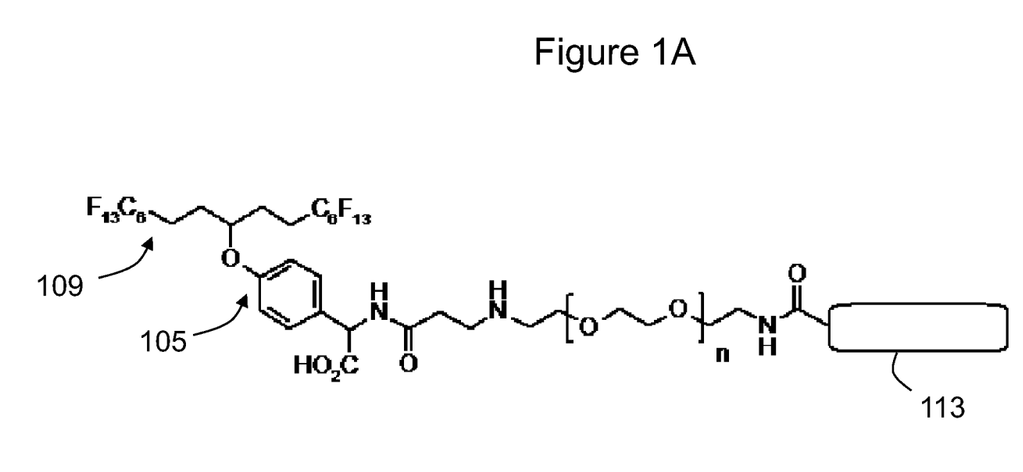
FIGS. 1A and 1B show exemplary fluorous-modified compositions according to the disclosure.
Figure 1B:
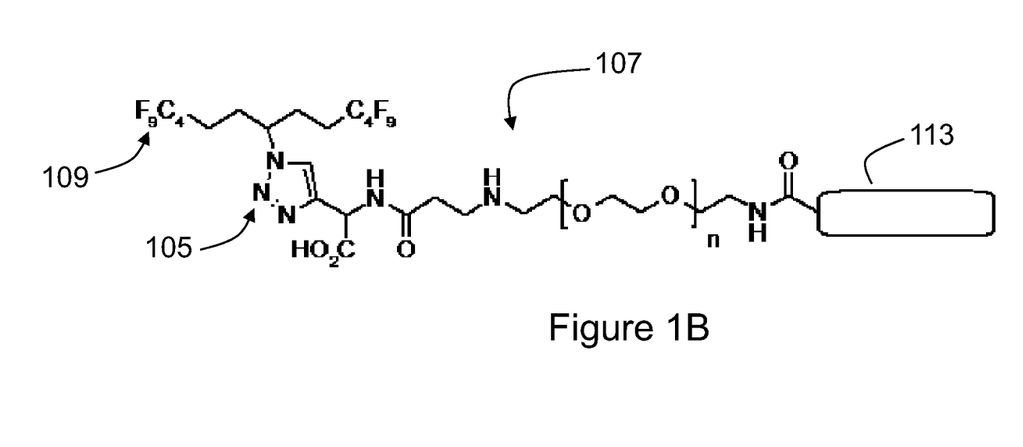

The fluorous-modified composition 105 includes a linker 107, a peptide 113 connected to the linker 107, and a fluorous domain 109 connected to the linker 107. As used herein, the term "connected" is direct or indirect and refers to covalent bonding, ion pairing, other close chemical associations, or a combination thereof. Embodiments of the fluorous-modified composition 105 may further include a solid-phase attachment group 111, may be devoid of the solid-phase attachment group 111, and/or may have any suitable combination of the linker 107 and the fluorous domain 109, for example, as is shown with the specific embodiments of the fluorous-modified composition 105 in FIGS. 1A and 1B. In one embodiment, the fluorous domain 109 and the linker 107 include other groups or moieties that provide reactive groups to covalently bond or ionically pair the linker 107, the fluorous domain 109, the peptide 113, or a combination thereof. Suitable reactive groups include, but are not limited to, carboxylic acids, amines, phosphines, alkynes, and azides.

The linker 107 connects components of the fluorous-modified composition 105. In one embodiment, the linker 107 includes or is a diamine linker. A non-limiting example of the linker 107 has the following molecular structure:

In one embodiment, the linker 107 has an n-value of between 0 and 5. In further embodiments, the linker 107 has an n-value of between 0 and 1, between 0 and 2, between 0 and 3, between 0 and 4, between 1 and 2, between 1 and 3, between 1 and 4, between 1 and 5, between 2 and 3, between 2 and 4, between 2 and 5, between 3 and 4, between 3 and 5, between 4 and 5, 1, 2, 3, 4, or 5.

Another non-limiting example of the linker 107 includes or has the following molecular structure:

In one embodiment, the linker 107 has an n-value of between 0 and 20. In further embodiments, the linker 107 has an n-value of between 0 and 20, between 0 and 5, between 0 and 10, between 0 and 15, between 5 and 10, between 5 and 15, between 5 and 20, between 10 and 15, between 10 and 20, 5, 10, 15, 20, or any suitable combination, sub-combination, range, or sub-range thereof.

A non-limiting example of the fluorous domain 109 includes or has the following molecular structure:

Another non-limiting example of the fluorous domain 109 includes or has the following molecular structure:

In one embodiment, the fluorous-modified composition 105 includes at least two or at least three terminal perfluoroalkyl groups in the fluorous domain 109 (for example, having the general formula of $C_nF_{2n+1}$). A non-limiting example of the fluorous domain 109, according to this embodiment, includes or has the following molecular structure:

Another non-limiting example of the fluorous domain 109, according to this embodiment, includes or has the following molecular structure:

Non-limiting examples of the solid-phase attachment group 111 include or portions of the solid-phase attachment group 111 carboxylic acid and dicarboxylic acid.

Figure 2:
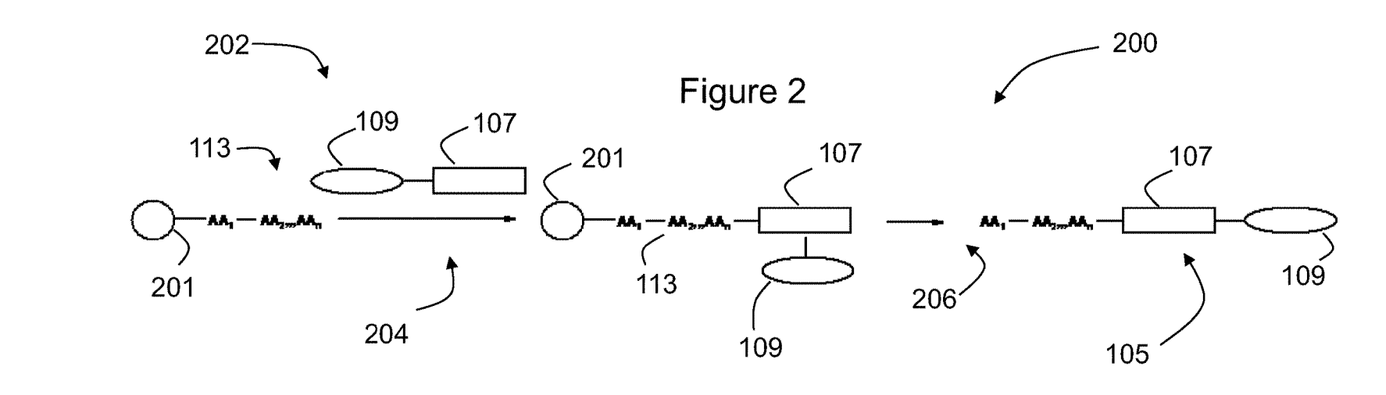
FIG. 2 shows a schematic view of an exemplary terminal tagging process according to the disclosure.
Figure 3:
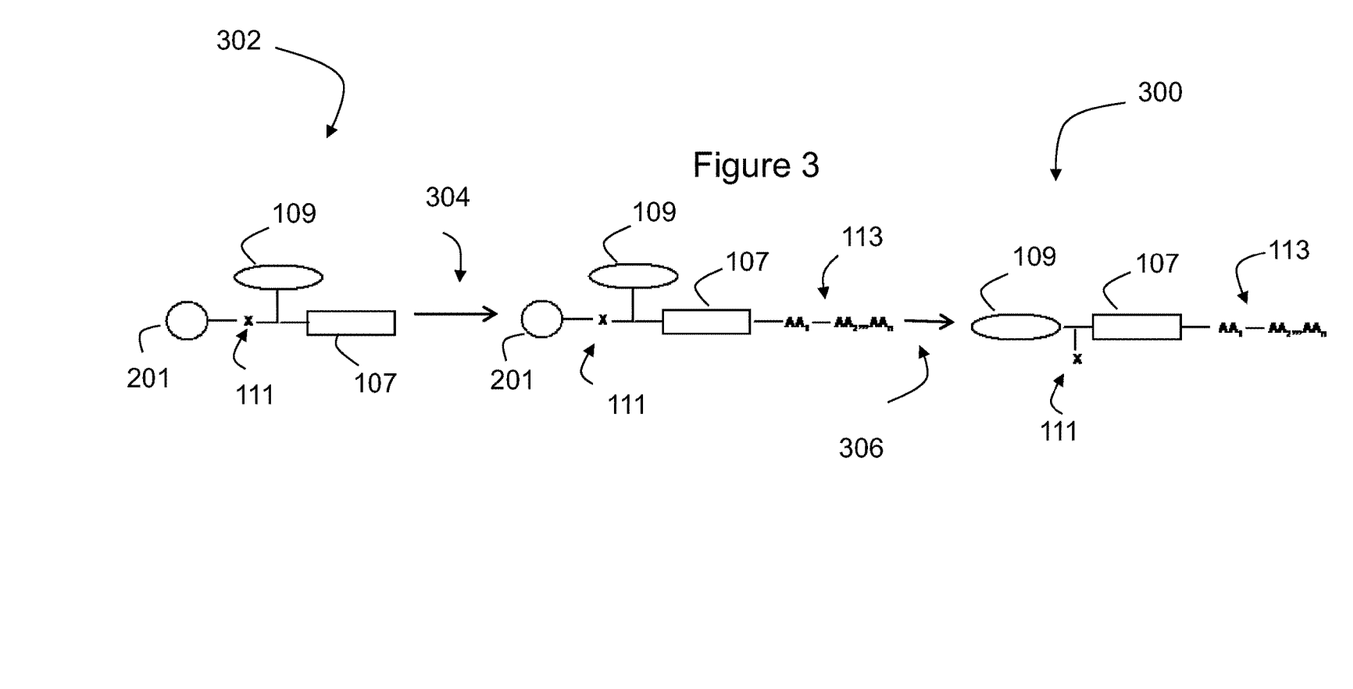
FIG. 3 shows a schematic view of an exemplary fluorous-loaded synthesis process according to the disclosure.

The fluorous-modified composition 105 is formed, for example, by a terminal tagging process 200 as shown in FIG. 2 and/or a fluorous loaded synthesis process 300 as shown in FIG. 3.

Referring to FIG. 2, in one embodiment, the terminal tagging process 200 includes providing a solid-phase resin 201 with a peptide 113 connected to and prepared on the solid-phase resin 201 (step 202). The linker 107 and fluorous domain 109 (such as, the fluorous domain 109 including, at least two terminal perfluoroalkyl groups in the fluorous domain 109 or at least three terminal perfluoroalkyl groups in the fluorous domain 109) connected to the linker 107 are attached to the peptide 113 (step 204), for example, by a covalent bond. The peptide 113 is cleaved from the solid-phase resin 201 (step 206), thereby forming the fluorous-modified composition 105.

Referring to FIG. 3, in one embodiment, the fluorous-loaded synthesis process 300 includes providing the solid-phase resin 201 (step 302). In this embodiment, the solid-phase resin 201 is connected to the solid-phase attachment group 111 that is connected to the fluorous domain 109 and the linker 107, for example, by a cleavable covalent bond. The peptide 113 is prepared through iterative solid phase peptide synthesis applied to the linker 107 (step 304) and the solid-phase resin 201 is cleaved from the solid-phase attachment group 111 (step 306), thereby forming the fluorous-modified composition 105.

Figure 4:
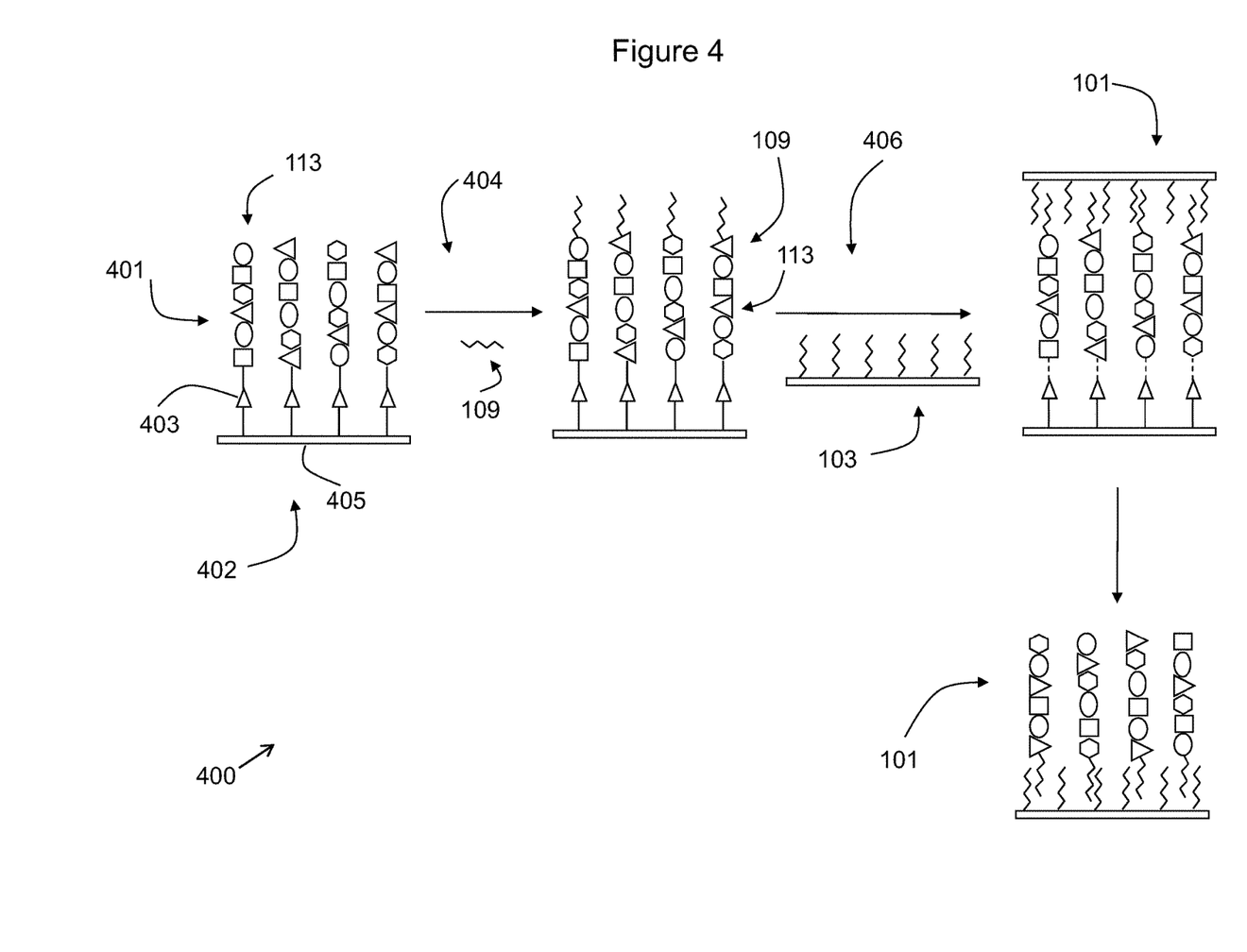
FIG. 4 shows a schematic view of an exemplary process of forming an exemplary fluorous peptide microarray according to the disclosure.

FIG. 4 shows an embodiment of a process 400 of forming the fluorous peptide microarray 101. The process 400 includes providing an array 401 (step 402). The array 401 includes at least one cleavable linker 403 connecting a solid-phase surface 405 to one or more of the peptides 113. The fluorous domain 109 is applied to the peptide(s) 113 (step 404) and the covalently-modified conductive fluorous surface 103 is applied under cleaving conditions (step 406), thereby forming the fluorous peptide microarray 101. The covalently-modified conductive fluorous surface 103 may be the same as or different from the covalently-modified conductive fluorous surface 103 shown and described in reference to FIG. 1.

Figure 5:
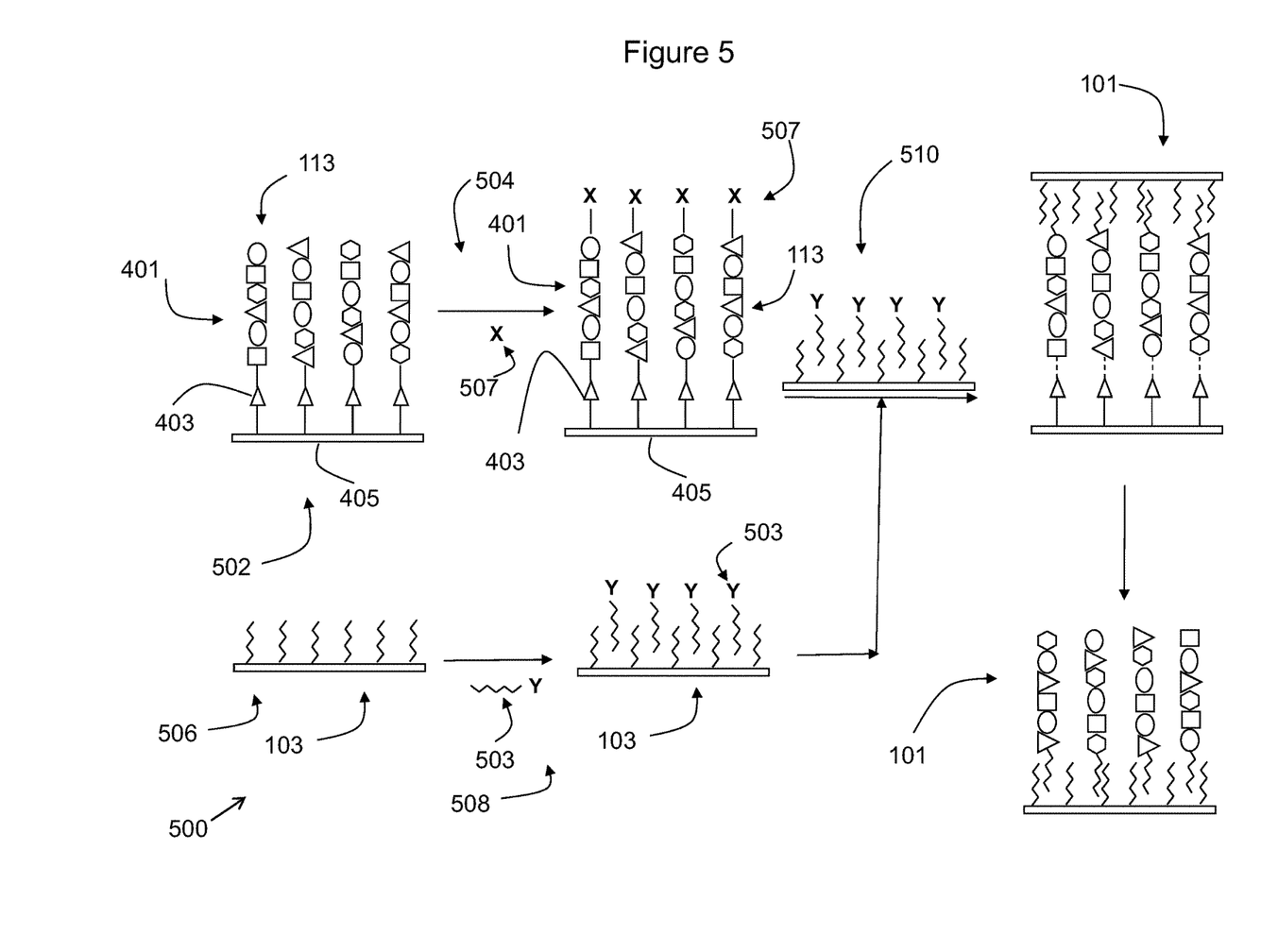
FIG. 5 shows a schematic view of an exemplary process of forming an exemplary fluorous peptide microarray according to the disclosure.

FIG. 5 shows an embodiment of a pre-coat process 500 of forming the fluorous peptide microarray 101. The process 500 includes providing an array 401 (step 502). The array 401 includes at least one cleavable linker 403 connecting a solid-phase surface 405 to one or more of the peptides 113. A reactive group 507 is applied to the peptide(s) 113 (step 504). Separately, the covalently-modified fluorous conductive surface 103 is provided (step 506) and a fluorous-modified reactive group 503 is applied to the covalently-modified conductive fluorous surface 103 (step 508), thereby forming an embodiment of the covalently-modified conductive fluorous surface 103 with the fluorous-modified reactive group 503 immobilized within by fluorous partitioning. The covalently-modified conductive fluorous surface 103 is applied to the array 401 under simultaneous reactive-cleaving conditions (step 510), thereby forming the fluorous peptide microarray 101 by concomitant cleavage from solid-phase surface 405 and reaction between the reactive group 507 and the fluorous-modified reactive group 503 to form array 101. The covalently-modified conductive fluorous surface 103 may be the same as or different from the covalently-modified conductive fluorous surface 103 shown and described in reference to FIG. 1.

Referring again to FIG. 1, in one embodiment, the process 100 of forming the fluorous peptide microarray 101 further includes enzyme modification of the peptide 113 (step 106). The content of the fluorous peptide microarray 101 is adjustable depending upon the protein or enzyme and an assay of interest. The enzyme modification may include using any suitable enzyme capable of mediating a chemical reaction or modification of another protein. Suitable enzymes include, but are not limited to, histone deactylases, histone methyltransferases, histone readers, sirtuins, kinases, enzymes associated with cancer, enzymes associated with Alzheimer's, enzymes associated with diabetes, other suitable enzymes, phosphatases, proteases, histone modifying enzymes, esterases, glycosyl transferases, hydrolases, other enzymes capable of facilitating posttranslational modifications, or combinations thereof.

Figure 6:
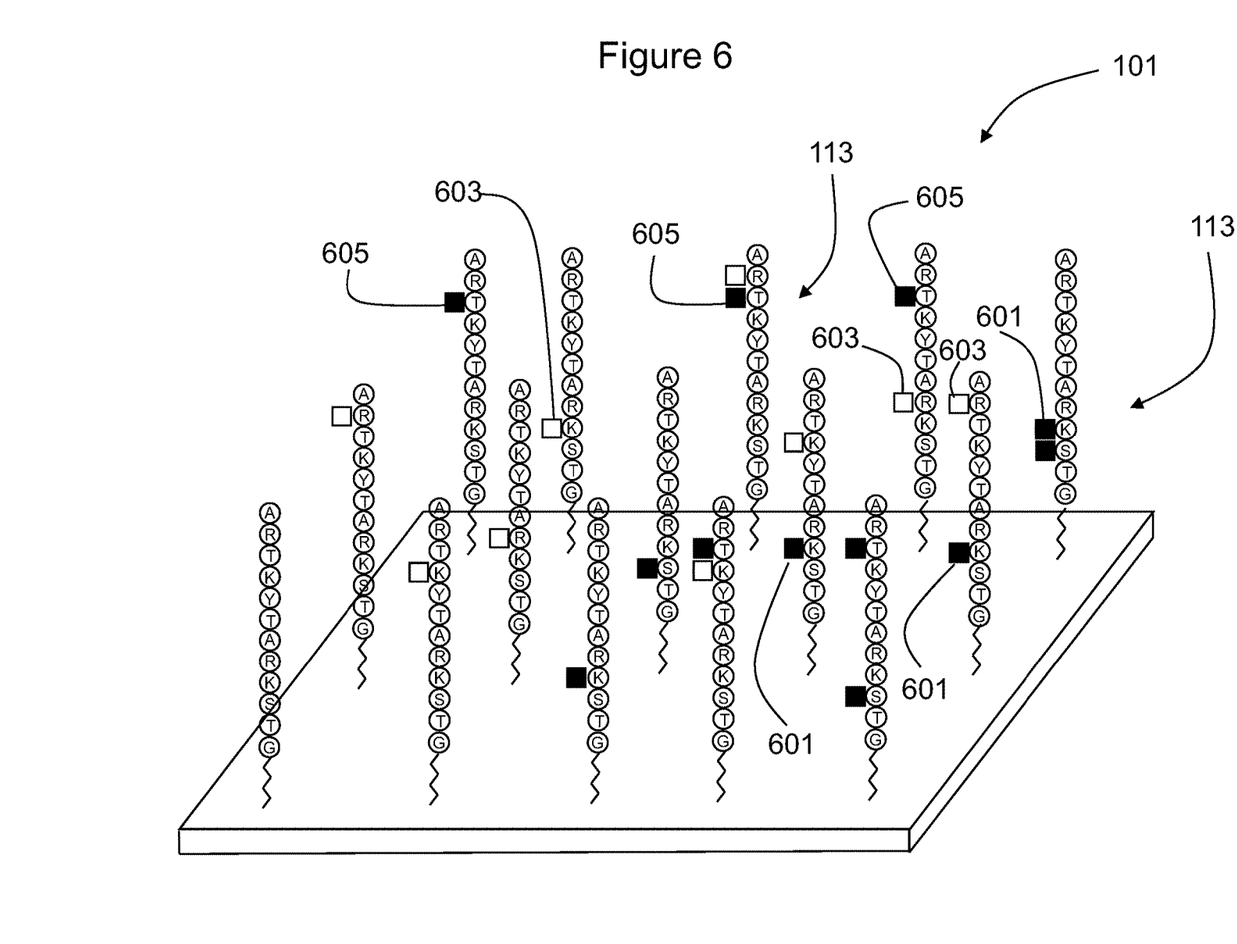
FIG. 6 shows a schematic view of an exemplary fluorous peptide microarray according to the disclosure.

FIG. 6 shows an embodiment of the fluorous peptide microarray 101. The fluorous peptide microarray 101 includes a plurality of the fluorous peptides 113 having various numbers and types of modifications. The modifications are additions, deletions, or modifications, to amino acid side chains of the histone tail peptide sequence. Suitable modifications include, but are not limited to, methylation, acetylation, phosphorylation, g-lycosylation, citrullation, ubiquitation, and summoylation. Generally, the modifications occur singly or in multiple combinations on the histone tails and are integral to gene expression and, thus, various disease states. The peptides 113 are arrayed on the surface as unmodified, a single modification, with a plurality of modifications, or a combination thereof. The peptides 113 in the fluorous peptide microarray 101 may include portions of native histone tails sequences that are unmodified or contain histone modifications selected from the group consisting of actylation 601, methylation 603, phosphorylation 605, other suitable histone modifications (for example, those described above), and combinations thereof.

In one embodiment, the fluorous peptide microarray 101 includes a series or library of fluorous-modified peptide sequences which are immobilized in a spatially segregated defined pattern onto a fluorous-modified surface.

Figure 7:
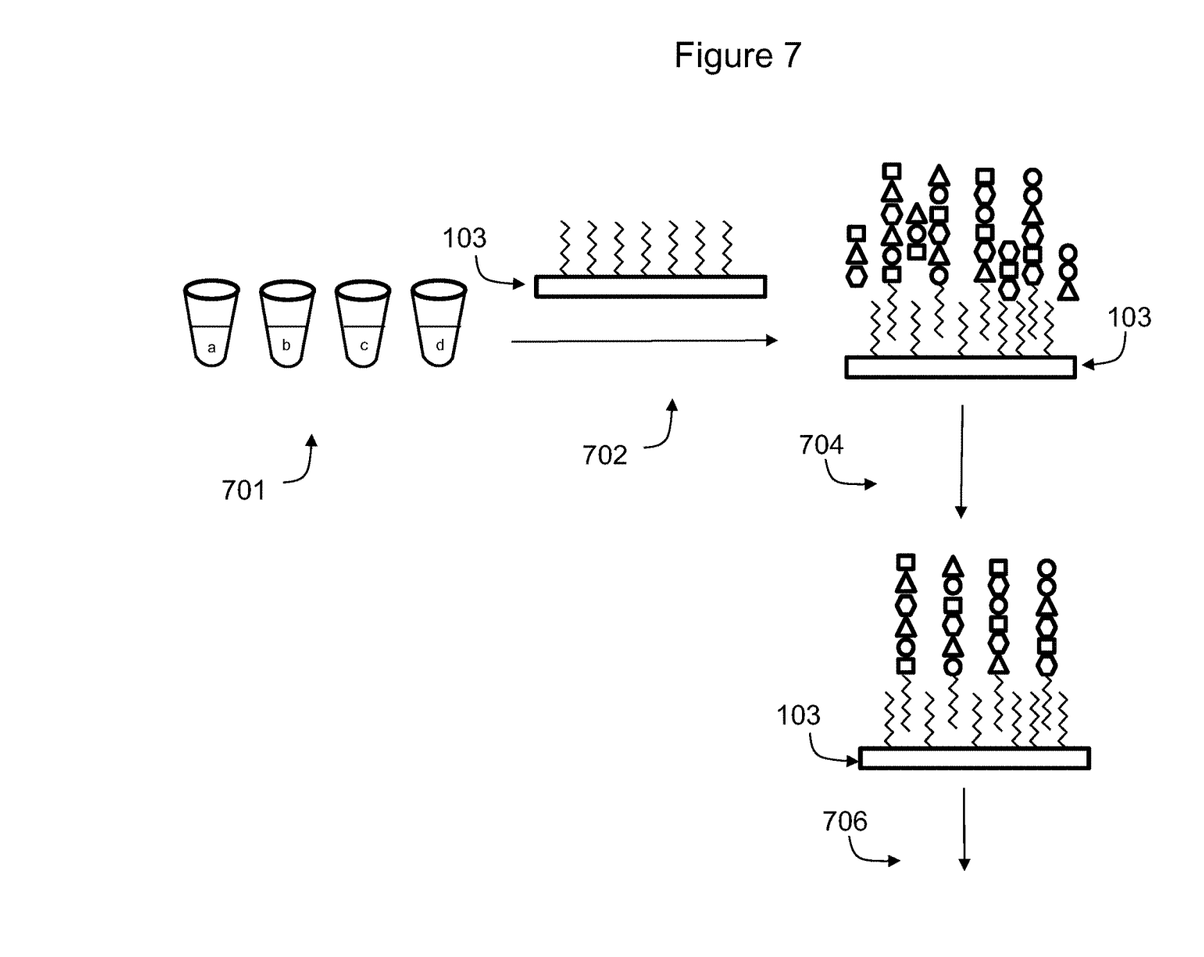
FIG. 7 shows a schematic view of an exemplary process of forming an exemplary fluorous peptide microarray according to the disclosure.

Referring to FIG. 7, in one embodiment, the fluorous peptide microarray 101 is formed by deposition (step 702), for example, spot deposition, of aliquots (a, b, c, and d) of a reaction mixture 701 containing the fluorous-modified composition 105 having the fluorous tagged peptides. The fluorous tagged peptides are immobilized on the covalently-modified conductive fluorous surface 103, while other reaction components are not immobilized. The fluorous conductive surface 103 with the immobilized fluorous peptides is then washed (step 704) to remove the non-immobilized components resulting in analyte enrichment, prior to mass spectrometry analysis (step 706).

In one embodiment, the fluorous peptide microarray 101 includes features corresponding to being formed through deposition of fluorous tagged peptide sequences that are prepared using blotting fluorous-modified peptides (for example, mimicking histone tails) or other techniques that had been prepared in situ on a non-fluorous surface.

In one embodiment, the fluorous peptide microarray 101 includes a chemically inert surface suitable for mass production (in contrast to SAMDI surfaces).

The content of the fluorous peptide microarray 101 is adjustable depending upon the protein or enzyme and assay of interest. Suitable enzyme classes included, but are not limited to, kinases, phosphatases, proteases, histone modifying enzymes, esterases, glycosyl transferases, hydrolases, or combinations thereof.

Any suitable enzyme capable of mediating a chemical reaction or modification of another protein may be investigated using the fluorous peptide microarray 101. The types of assays that can be conducted include epitope mapping, substrate profiling, selectivity and activity determination, inhibition assays, protein binding, and counterscreens.

Referring again to FIG. 1, in one embodiment, compositional detection is performed (step 108). The compositional detection (step 108) may be performed as part of the process 100 shown in FIG. 1 or independently. The compositional detection (step 108) includes mass spectrometry analysis using the fluorous peptide microarray 101. Additionally or alternatively, the compositional detection (step 108) includes other analytical methods.

In one embodiment, the compositional detection (step 108) includes analyzing marks, for example, by using mass spectrometry, without the addition of a matrix. In one embodiment, the composition detection (step 108) identifies information about the modifications on the histone tails. The information is gathered and/or used (step 110). In one embodiment, the information includes direct readouts, data, plots, chromatograms 115, or combinations thereof corresponding to the peptides 113 of the fluorous peptide microarray 101. The use (step 110) of the information includes transmitting the information, receiving the information, relying upon the information, instructing others based upon the information, or a combination thereof.

In one embodiment, the compositional detection (step 108) corresponds with the fluorous peptide microarray 101 having been incubated with a test solution (for example, including or not including the enzymes and/or proteins), thereby forming the modifications, such as in the presence of purified histone enzymes or cell lysates containing such enzymes results in a structural change (for example, addition, elimination, or isomerization of some or all of the modifications). The modifications may be interrogated by laser desorption/ionization and analyzed by the mass spectrometry, for example, to confirm that a change in the peptide 113 has taken place due to action of the enzyme and/or the protein or that an enzyme and/or protein-ligand binding complex has been formed. The compositional detection (step 108) may further provide information regarding amino acid residue on which an enzymatic reaction took place.

The types of assays that can be conducted include epitope mapping, substrate profiling, compound screening, selectivity and activity determination, inhibition assays, protein binding and counterscreens.

While only certain features and embodiments of the invention have been shown and described, many modifications and changes may occur to those skilled in the art (for example, variations in sizes, dimensions, structures, shapes and proportions of the various elements, values of parameters (for example, temperatures, pressures, etc.), mounting arrangements, use of materials, colors, orientations, etc.) without materially departing from the novel teachings and advantages of the subject matter recited in the claims. The order or sequence of any process or method steps may be varied or re-sequenced according to alternative embodiments. It is, therefore, to be understood that the appended claims are intended to cover all such modifications and changes as fall within the true spirit of the invention. Furthermore, in an effort to provide a concise description of the exemplary embodiments, all features of an actual implementation may not have been described (i.e., those unrelated to the presently contemplated best mode of carrying out the invention, or those unrelated to enabling the claimed invention). It should be appreciated that in the development of any such actual implementation, as in any engineering or design project, numerous implementation-specific decisions may be made. Such a development effort might be complex and time consuming, but would nevertheless be a routine undertaking of design, fabrication, and manufacture for those of ordinary skill having the benefit of this disclosure, without undue experimentation.

What is claimed is:

1. A microarray for detecting targets and biomolecule interactions, comprising:
   (a) a covalently-modified electrically conductive fluorous surface comprising a compositional grid,
      (i) wherein the surface is electrically conductive with a sheet resistivity of less than 50 ohms/square, and
      (ii) wherein the electrically conductive surface is a perfluorocarbon modified;
   (b) a plurality of fluorous-modified peptide compositions, wherein each fluorous-modified peptide composition in the plurality of fluorous-modified peptide compositions includes:
      (i) a terminal fluorous domain or tag comprising at least one perfluoroalkyl groups in the fluorous domain or tag, wherein the terminal fluorous domain or tag immobilizes each fluorous-modified peptide composition on the perfluorocarbon covalently-modified electrically conductive surface by non-covalently interacting with the perfluorocarbon modified surface through fluorous partitioning, wherein each fluorous-modified peptide composition individually occupies a defined location within the grid,
      (ii) a diamine linker connected to the terminal fluorous domain or tag; and
      (iii) a peptide connected to the diamine linker, wherein the peptide is configured to bind targets and interact with biomolecules of interest;
   (c) wherein the presence of a target bound to the peptide in the fluorous-modified peptide composition or biomolecule interaction with the peptide in the fluorous-modified peptide composition is detectable by mass spectrometry through individual laser ionization of the peptide fluorous-modified composition immobilized on the perfluorocarbon covalently-modified electrically conductive surface.

2. The microarray of claim 1, wherein the perfluorocarbon modified surface includes a fluorous-modified indium tin oxide, a fluorous-modified silicon black, or a combination thereof.

SEQUENCE LISTING

```
<160> NUMBER OF SEQ ID NOS: 1

<210> SEQ ID NO 1
<211> LENGTH: 12
<212> TYPE: PRT
<213> ORGANISM: Homo sapiens
<220> FEATURE:
<221> NAME/KEY: METHYLATION
<222> LOCATION: (2)..(9)
<223> OTHER INFORMATION: The Arginine at position (2) and/or position
      (8), and/or the Lysine at position (4) and/or position (9) may
      be methylated.
<220> FEATURE:
<221> NAME/KEY: PHOSPHORYLATION
<222> LOCATION: (3)..(10)
<223> OTHER INFORMATION: The Threonine at position (3) and/or the Serine
      at position (10) may be phosphorylated.
<220> FEATURE:
<221> NAME/KEY: ACETYLATION
<222> LOCATION: (9)..(9)
<223> OTHER INFORMATION: The Lysine at position (9) may be acetylated

<400> SEQUENCE: 1

Ala Arg Thr Lys Tyr Thr Ala Arg Lys Ser Thr Gly
1               5                   10
```

3. The microarray of claim 1, wherein the peptide in each fluorous-modified peptide composition is adapted to undergo enzyme modification.

4. The microarray of claim 1, wherein the peptide in each fluorous modified peptide composition is configured to interact with kinases, proteases, glycosyl transferases, phosphatases, histone modifying enzymes, or a combination thereof.

5. The microarray of claim 1, wherein the peptide in each fluorous modified peptide composition is an irreversible binding partner for interacting with proteins or protein complexes.

6. The microarray of claim 1, wherein the peptide in each fluorous modified peptide composition is a reversible binding partner for interacting with proteins or protein complexes.

7. The microarray of claim 1, wherein the mass spectrometry further includes matrix assistance analysis methods, matrix-free analysis methods, or a combination thereof.

8. The microarray of claim 1, wherein the microarray detects a change in mass of a fluorous-modified composition through action of an enzyme by mass spectrometry.

9. The microarray of claim 1, wherein the microarray detects a change in mass of a fluorous-modified composition through binding of a protein by mass spectrometry.

10. The microarray of claim 1, wherein the targets include proteins and enzymes, and wherein the biomolecule interactions include enzymatic modification of the peptides in the fluorous-modified compositions.

11. The microarray of claim 1, wherein the peptide in each fluorous-modified peptide compositions interact with a target or biomolecule after the immobilization of the fluorous-modified compositions on the perfluorocarbon modified electrically conductive surface.

12. The microarray of claim 1, wherein the peptide in each fluorous-modified peptide compositions interact with a target or biomolecule prior to the immobilization of the fluorous-modified compositions on the perfluorocarbon modified electrically conductive surface.

13. The microarray of claim 1, wherein the perfluorocarbon modified electrically conductive surface is washed prior to mass spectrometry to selectively retain the fluorous-modified compositions having bound targets or biomolecule interactions.

14. The microarray of claim 1, wherein the microarray is used to detect information, and wherein the information includes the presence of bound targets, the presence of biomolecule interactions, or a combination thereof.

15. The microarray of claim 1, further comprising a solid-phase attachment group connected to the linker within the fluorous-modified compositions.

* * * * *